US012622707B1

(12) United States Patent
Hasson

(10) Patent No.: US 12,622,707 B1
(45) Date of Patent: May 12, 2026

(54) SURGICAL SPLASH GUARD AND METHODS OF USE

(71) Applicant: DWCH Holdings, Inc., Newport Beach, CA (US)

(72) Inventor: Duke Hasson, Corona del Mar, CA (US)

(73) Assignee: DWCH Holdings, Inc., Newport Beach, CA (US)

( * ) Notice: Subject to any disclaimer, the term of this patent is extended or adjusted under 35 U.S.C. 154(b) by 0 days.

(21) Appl. No.: 19/268,553

(22) Filed: Jul. 14, 2025

(51) Int. Cl.
*A61B 17/14* (2006.01)
*A61B 90/00* (2016.01)

(52) U.S. Cl.
CPC ............ *A61B 17/142* (2016.11); *A61B 90/05* (2016.02)

(58) Field of Classification Search
CPC ..... A61B 17/14; A61B 17/142; A61B 17/144; A61B 17/147; A61B 17/149; A61B 17/16; A61B 17/1613; A61B 17/1633; A61B 17/1635; A61B 17/1637; A61B 17/164; A61B 17/1642; A61B 17/1644; A61B 17/1646; A61B 17/1655; A61B 17/1657; A61B 17/1659; A61B 17/1662; A61B 17/1664; A61B 17/1666; A61B 17/1668; A61B 17/1671; A61B 17/1673; A61B 17/1675; A61B 17/677; A61B 17/1679; A61B 17/1682; A61B 17/1684; A61B 17/1686; A61B 17/1688; A61B 17/1691; A61B 17/1693; A61B 17/1695; A61B 17/1697; A61B 90/05
See application file for complete search history.

(56) References Cited

U.S. PATENT DOCUMENTS

| | | | | |
|---|---|---|---|---|
| 4,848,322 A | * | 7/1989 | Dash | A61B 90/05 128/857 |
| 4,949,734 A | * | 8/1990 | Bernstein | A61B 90/05 128/897 |
| 4,976,254 A | * | 12/1990 | Dash | A61B 90/05 128/857 |
| 5,220,753 A | * | 6/1993 | Whitman | B24B 55/10 451/456 |
| 5,275,559 A | * | 1/1994 | Rihel | A61C 1/16 433/116 |
| 5,542,435 A | * | 8/1996 | Kelly | A61B 17/3201 128/846 |

(Continued)

FOREIGN PATENT DOCUMENTS

| | | | | | |
|---|---|---|---|---|---|
| CN | 113040859 A | * | 6/2021 | | A61B 90/05 |
| CN | 119587110 A | * | 3/2025 | | A61B 90/05 |

(Continued)

*Primary Examiner* — Eric S Gibson
(74) *Attorney, Agent, or Firm* — Fish IP Law, LLP

(57) ABSTRACT

A splash guard for use with a surgical tool includes a shield and a coupling mechanism configured to removably couple the shield to the surgical tool body. The coupling mechanism cooperates with the shield such that during operation of the saw, the shield is not centered within a plane defined by the reciprocating motion of the saw blade. The shield can be formed from a clean shrink wrap supported by a frame. The coupling mechanism can include a rotatable clip coupling with detents for predefined positions. The splash guard can be configured to fit straight or angled surgical saws and is sterilized and disposable.

9 Claims, 3 Drawing Sheets

(56) References Cited

U.S. PATENT DOCUMENTS

| | | | | |
|---|---|---|---|---|
| 5,787,893 | A * | 8/1998 | Hoftman | G02B 3/08 |
| | | | | 128/846 |
| D399,971 | S * | 10/1998 | Scherer | A61B 90/05 |
| | | | | D24/231 |
| 6,001,115 | A * | 12/1999 | Ahola | A61B 17/144 |
| | | | | 606/176 |
| 6,210,261 | B1 * | 4/2001 | Johnson | B24B 55/052 |
| | | | | 451/457 |
| 6,561,887 | B2 * | 5/2003 | Lai | B24B 27/08 |
| | | | | 403/362 |
| 6,716,215 | B1 * | 4/2004 | David | A61B 17/1622 |
| | | | | 433/116 |
| 8,663,173 | B2 * | 3/2014 | Wheeler | A61M 5/3202 |
| | | | | 604/192 |
| 9,427,288 | B1 * | 8/2016 | Chenger | A61B 90/05 |
| 10,363,113 | B1 * | 7/2019 | Chenger | A61B 50/30 |
| 10,531,889 | B2 * | 1/2020 | Husk | A61B 90/05 |
| 11,049,626 | B1 * | 6/2021 | Ahearn | A61B 90/05 |
| 11,141,816 | B2 * | 10/2021 | Neveu | B23K 26/354 |
| 11,950,963 | B2 * | 4/2024 | Tanner | A61B 90/05 |
| 2006/0292522 | A1 * | 12/2006 | Lees | A61C 17/005 |
| | | | | 433/116 |
| 2007/0173773 | A1 * | 7/2007 | Stamler | A61B 90/05 |
| | | | | 128/898 |
| 2011/0313370 | A1 * | 12/2011 | Smyth | B29C 66/861 |
| | | | | 604/263 |
| 2012/0157778 | A1 * | 6/2012 | Wheeler | A61M 25/02 |
| | | | | 600/201 |
| 2014/0220292 | A1 * | 8/2014 | Smyth | A61B 5/150274 |
| | | | | 29/428 |
| 2016/0027540 | A1 * | 1/2016 | Gordon | G21F 1/02 |
| | | | | 250/515.1 |
| 2016/0128780 | A1 * | 5/2016 | Husk | A61B 17/3201 |
| | | | | 606/174 |
| 2016/0220199 | A1 * | 8/2016 | Gordon | A61B 6/107 |
| 2018/0279802 | A1 * | 10/2018 | Burnside | A47D 15/005 |
| 2021/0321885 | A1 * | 10/2021 | Zaugg | A61B 90/40 |
| 2021/0338362 | A1 * | 11/2021 | Tanner | A61B 90/57 |
| 2021/0353380 | A1 * | 11/2021 | Sellars | A61B 90/50 |
| 2022/0142269 | A1 * | 5/2022 | Orrington, II | A61C 19/00 |
| 2023/0032583 | A1 * | 2/2023 | Sarin | A61B 17/8822 |
| 2023/0373369 | A9 * | 11/2023 | Orrington, II | A61G 15/00 |

FOREIGN PATENT DOCUMENTS

| | | | | | |
|---|---|---|---|---|---|
| DE | 102020118729 | A1 * | 11/2021 | | A61C 17/14 |
| DE | 102021000116 | A1 * | 7/2022 | | A61B 90/05 |
| WO | WO-2009077695 | A2 * | 6/2009 | | A61B 90/05 |

* cited by examiner

300

120

310

110

130

320

400

110

120

230

420

410

SURGICAL SPLASH GUARD AND METHODS OF USE

FIELD OF THE INVENTION

The field of the invention is surgical tools.

BACKGROUND

The following background discussion includes information that may be useful in understanding the present invention. It is not an admission that any of the information provided herein is prior art or relevant to the presently claimed invention, or that any publication specifically or implicitly referenced is prior art.

Surgical saws are commonly employed in orthopedic and surgical procedures to cut bones or tissue with precision and speed. However, the high-speed oscillation of the saw blade often results in the generation and dissemination of fluids, bone particles, and biological debris. This presents a contamination risk and a safety concern for surgical personnel.

Existing rigid shields or custom blade guards may require complex installation, may not be adaptable across different saw geometries, or may lack features that maintain sterilization and case of disposal. For example, U.S. Pat. No. 6,001,115 to Ahola et al. discloses a blade guard designed to shield an operator's tissue from being cut, while also assisting in bone separation during cutting. U.S. Pat. No. 3,972,332 to Wakim describes a transparent shield held above the surgical field to intercept airborne debris.

Despite these various approaches to splash guards, there is still a need for a simplified splash guard system that provides a sterile barrier between the surgical site and the surrounding environment, reduces contamination, is adaptable to both straight and angled saw configurations, and capable of being positioned outside the plane of reciprocating blade motion to effectively block debris.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The recitation of ranges of values herein is merely intended to serve as a shorthand method of referring individually to each separate value falling within the range. Unless otherwise indicated herein, each individual value is incorporated into the specification as if it were individually recited herein, and ranges include their endpoints.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as" provided with respect to certain embodiments herein is intended merely to better illuminate the invention and does not pose a limitation on the scope of the invention otherwise claimed. No language in the specification should be construed as indicating any non-claimed element essential to the practice of the invention. Unless a contrary meaning is explicitly stated, all ranges are inclusive of their endpoints, and open-ended ranges are to be interpreted as bounded on the open end by commercially feasible embodiments.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

The present invention provides a splash guard for use with surgical tools having a body and a saw blade.

In preferred embodiments the splash guard comprises a shield, which is preferably injected molded using a suitable plastic such as Lexan™ polycarbonate. Other materials can be used, including for example a shrink wrap material. Shields can be sterilized and packaged in a sterile pouch for single use disposal to reduce contamination risk.

A coupling mechanism is configured to removably couple the shield to the surgical tool body. Unlike prior art shields, the coupling mechanism cooperates with the shield such that during operation of the saw, the shield is not centered within the plane defined by the reciprocating motion of the saw blade. Contemplated coupling mechanisms include a clip coupling, and especially a rotatable clip coupling that allows the splash guard to be rotated to different positions around the tool body. A pivot can be positioned between the shield and the coupling mechanism, such that when the pivot is aligned parallel to the direction of the saw blade, the shield can be rotated relative to the coupling for optimal splash protection.

Also in preferred embodiments, splash guards comprise a wire or other frame disposed about the perimeter of the shield. Contemplated splash guards can also comprise a unitary shield, for example an injection molded plastic without a frame. Shields are preferably distanced approximately 6 to 12 cm from the closest portion of the blade.

In some embodiments, the splash guard includes detents to restrict rotation of the clip coupling to predefined angular positions, improving stability during use.

Embodiments of the claimed splash guard can be used with many types of reciprocating saw blades, including straight surgical saws or angled surgical saws.

In another aspect, the inventive subject matter provides methods of conducting a surgical operation using the contemplated splash guards. The method includes removing a splash guard from its container, attaching the splash guard to a surgical tool using a clip coupling, rotating the shield or clip coupling to a desired position, using the surgical tool with the splash guard attached to perform an operation, removing the splash guard from the surgical tool, and disposing of the removed splash guard.

The inventive subject matter addresses the need for a sterile, disposable, rotatable splash guard system that enhances safety and sterility across various surgical tools

DETAILED DESCRIPTION

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other and indirect coupling (in which at least one additional element is located between the two elements. Therefore, the terms "coupled to" and "coupled with" are used synonymously.

Figures 1A, 1B:
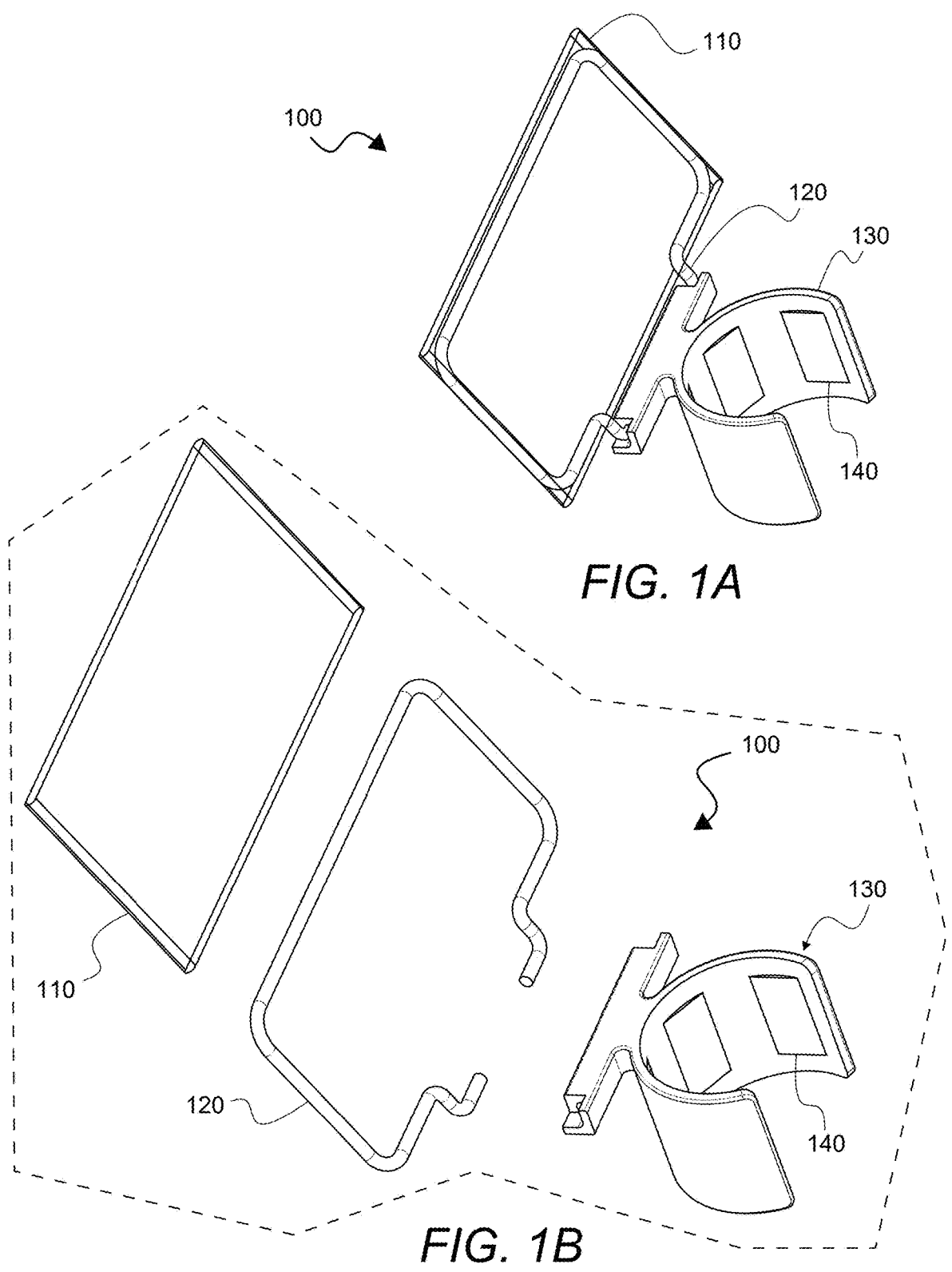
FIGS. 1A and 1B are a perspective view of the splash guard.

FIGS. 1A and 1B generally illustrate a splash guard 100 comprising a guard wrap 110, a guard frame 120, and a coupling 130.

The guard wrap 110 serves as the shield, and can be formed from a poly bag or shrink wrap material, or any other suitable material, including other plastics or glass. An advantage of using shrink wrap is that it is lightweight, flexible, and cost-effective, allowing disposable single-use sterile packaging while providing sufficient barrier protection against splashes, fluids, and debris generated during surgical cutting.

The guard frame 120 is preferably made of a suitably stiff material such as ASTM 228 music wire.

Clip coupling 130 is preferably a clip-type coupling that is sufficiently rigid to hold the guard frame 120 in place, but flexible enough to clip on and off a receiving portion of the body of the tool. Clip coupling 130 can be fabricated via injection molding of 8033G Nylon. Clip coupling 130 can include detents 140, which restrict rotation of clip coupling 130 about the surgical tool body.

Figure 2A:
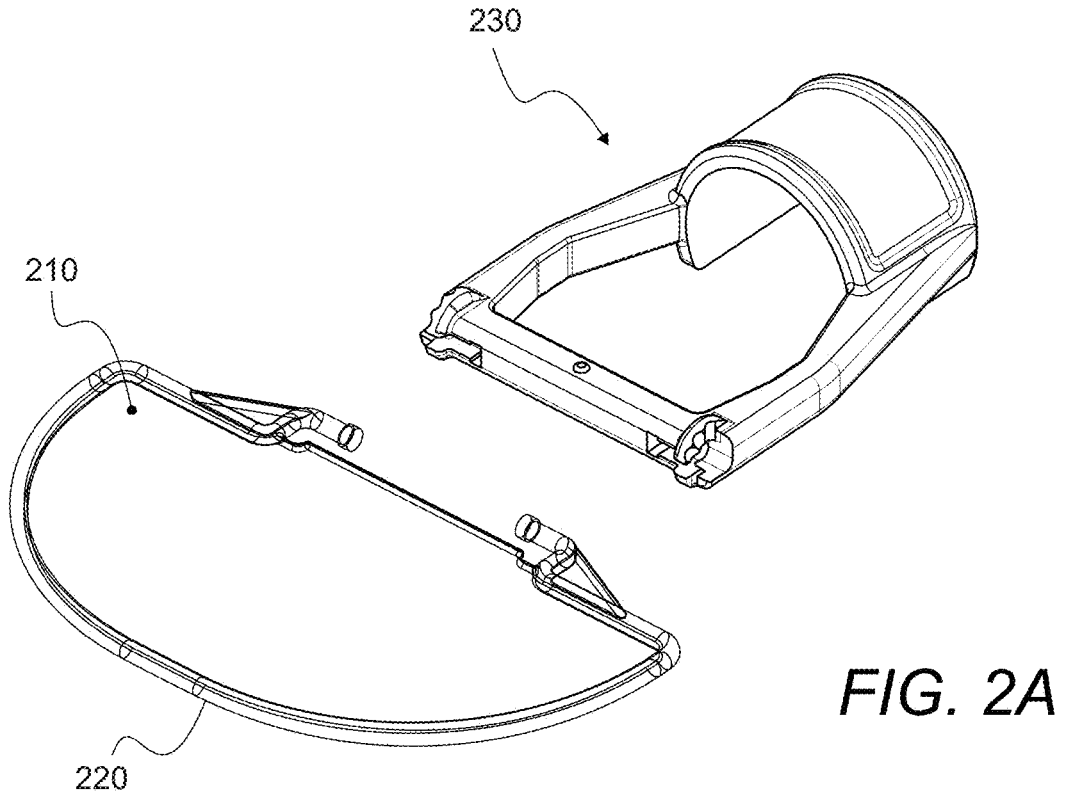
FIGS. 2A and 2*b* depict a splash guard assembly
Figure 2B:
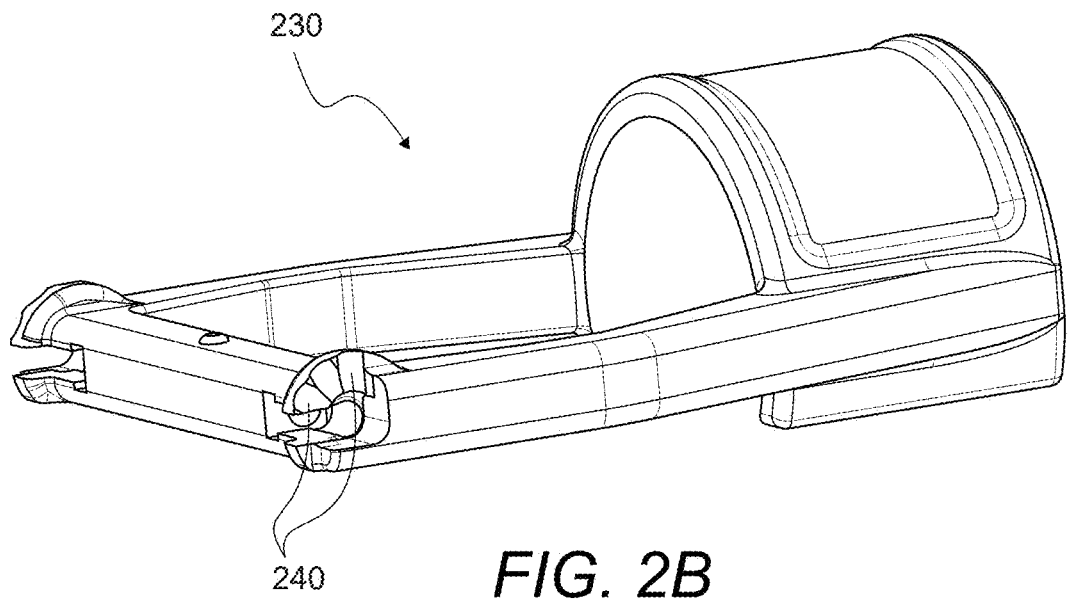

FIGS. 2A and 2B depict an alternative embodiment of the splash guard 200 comprising guard wrap 210, a guard frame 220, and a coupling 230.

The guard wrap 210 serves as the shield and can be formed from a poly bag or shrink wrap material, providing the same benefits described above.

The guard frame 220 is preferably made of a suitably stiff material such as ASTM 228 music wire and includes snap means at its ends for secure attachment to the surgical tool body to the coupling 230.

Clip coupling 230 is preferably a rotatable clip-type coupling with an arm configured to clip on and off the body of the surgical tool (210). Slots or detents 240 disposed within the clip arm restrict rotation or movement of the splash guard relative to the surgical tool, enabling predefined angular positions such as 0°, 30°, 60°, and 90°. This feature allows surgeons to orient the splash guard for maximum splash protection while maintaining unobstructed saw blade operation.

Figure 3:
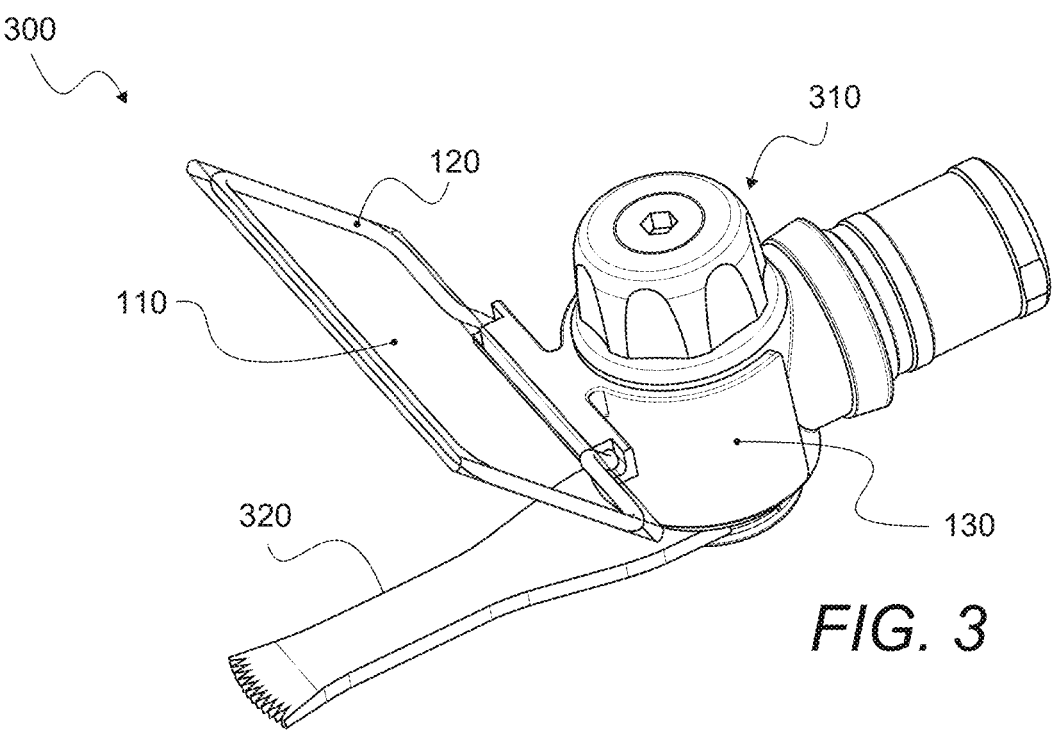
FIG. 3 illustrates an embodiment of the splash guard assembly configured for use with an angled surgical saw

FIG. 3 illustrates an embodiment of the splash guard 300 configured for use with an angled surgical saw, comprising a guard wrap 110, guard frame 120, a rotatable clip coupling 130 attached to the body of an angled surgical saw 310, and a saw head 320.

The clip coupling 130 accommodates the angled orientation of saw head 220 while maintaining the shield completely outside the plane of the reciprocating saw blade's motion for effective splash prevention. This off-plane configuration ensures the shield does not interfere with blade reciprocation. Off-plane placement allows the shield to remain lightweight and flexible, as it does not require structural reinforcement to withstand blade impacts, while still effectively intercepting debris ejected by the blade without obstructing the surgeon's view or access.

Figure 4:
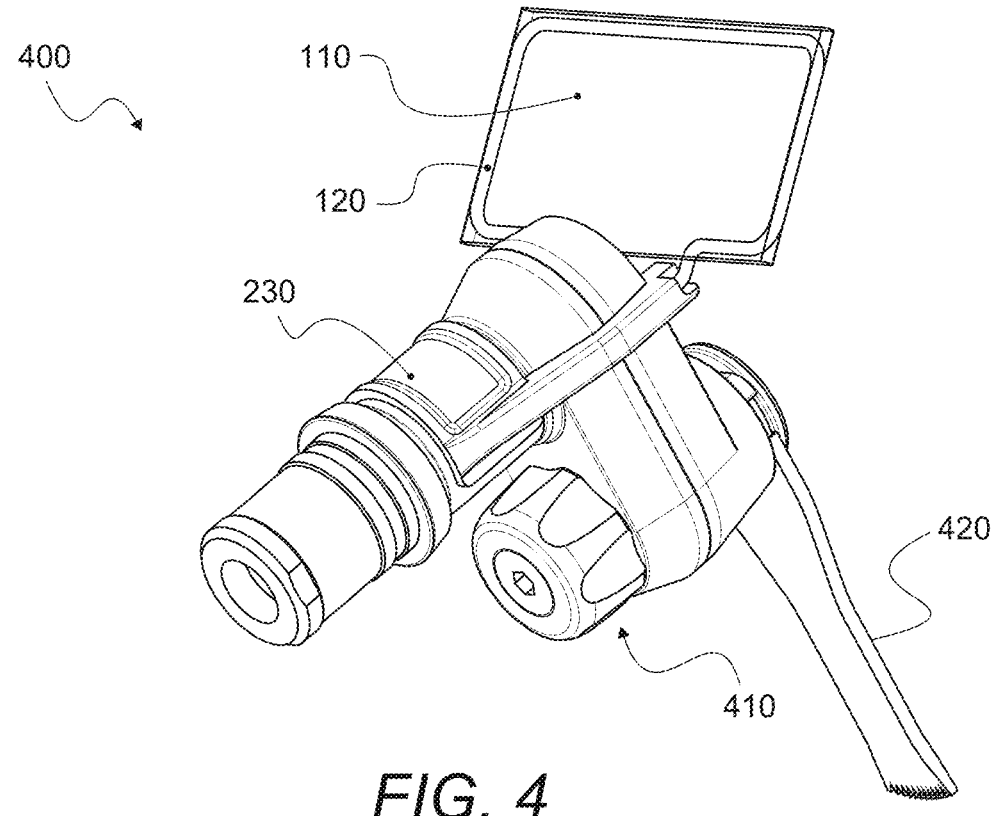
FIG. 4 illustrates an embodiment of the splash guard assembly configured for use with a straight surgical saw

FIG. 4 illustrates an embodiment of the splash guard 400 configured for use with a straight surgical saw, comprising a guard wrap 110, guard frame 120, rotatable clip coupling 230, and the body of a straight surgical saw 410 attached to the clip coupling and a saw head 420.

This assembly enables secure attachment to straight surgical saws, positioning the shield effectively while avoiding interference with the saw blade's cutting motion.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

I claim:

1. A cutting tool comprising: a splash guard, a body, and a saw blade, the splash guard comprising:
   a shield;
   a coupling mechanism configured to position the shield on the body and off-center from a plane defined by a reciprocating motion of the saw blade, wherein during operation of the saw blade, the shield is situated completely outside the plane defined by the reciprocating motion of the saw blade; and a pivot positioned between the shield and the coupling mechanism, the pivot aligned parallel to a direction of the saw blade.

2. The cutting tool of claim 1, wherein the saw blade is a reciprocating saw blade.

3. The cutting tool of claim 1, wherein the coupling mechanism is a clip coupling.

4. The cutting tool of claim 1, further comprising a frame disposed about a perimeter of the shield.

5. The cutting tool of claim 4, wherein the frame is distanced from a closest portion of the saw blade by 6 to 12 cm, inclusive.

6. The cutting tool of claim 1, wherein the splash guard is packaged in a sterile container comprising a pouch.

7. The cutting tool of claim 1, wherein the cutting tool is a straight surgical saw.

8. The cutting tool of claim 1, wherein the cutting tool is an angled surgical saw.

9. The cutting tool of claim 1, wherein the shield is sterilized.

* * * * *